United States Patent
Bui-Bertrand et al.

(10) Patent No.: US 6,238,681 B1
(45) Date of Patent: May 29, 2001

(54) SINGLE-PHASE TRANSPARENT AQUEOUS COSMETIC COMPOSITION

(75) Inventors: Lién Bui-Bertrand, Savigny sur Orge; Marie-Laure Carrel, Paris, both of (FR)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 09/358,255

(22) Filed: Jul. 20, 1999

(30) Foreign Application Priority Data

Jul. 21, 1998 (FR) .................................................. 98 09301

(51) Int. Cl.⁷ ............................... A61K 7/00; A61K 7/02; A61K 7/50
(52) U.S. Cl. ......................... 424/401; 510/136; 510/137; 514/844; 514/846
(58) Field of Search ............................ 424/401; 514/844, 514/846; 510/136, 137

(56) References Cited

U.S. PATENT DOCUMENTS

| | | | | |
|---|---|---|---|---|
| 4,323,468 | * | 4/1982 | Grollier et al. | 252/174.17 |
| 5,290,471 | * | 3/1994 | Greene et al. | 252/108 |
| 5,643,584 | * | 7/1997 | Farng et al. | 424/401 |
| 5,750,572 | * | 5/1998 | Bruzzese | 514/560 |
| 5,925,348 | * | 7/1999 | Riley et al. | 424/94.5 |
| 5,951,990 | * | 9/1999 | Ptchelintsev | 424/401 |
| 5,989,596 | * | 11/1999 | Bresson-Rival et al. | 424/711 |
| 5,993,793 | * | 4/1982 | Simon et al. | 424/70.31 |
| 6,080,393 | * | 11/1999 | Liu et al. | 424/78.03 |

FOREIGN PATENT DOCUMENTS

| | | |
|---|---|---|
| 2 358 148 | 2/1978 | (FR) . |
| WO 95/16661 | 6/1995 | (WO) . |
| WO 95/34540 | 12/1995 | (WO) . |

* cited by examiner

*Primary Examiner*—Shelley A. Dodson
*Assistant Examiner*—Marina Lamm
(74) *Attorney, Agent, or Firm*—Oblon, Spivak, McClelland, Maier & Neustadt, P.C.

(57) ABSTRACT

A single-phase transparent aqueous liquid cosmetic composition comprising at least 90% of water, at least one alkyl para-hydroxybenzoate (paraben), preferably methyl para-hydroxybenzoate (methylparaben), and at least one metabisulfite, preferably sodium metabisulfite. This composition is preferably devoid of primary alcohol. The inventive composition may be in the form of a stable transparent lotion and may be used, in particular, for gently cleaning and/or removing make-up from the skin and/or eyes. The present invention also relates to a process for dissolving an alkyl para-hydroxybenzoate in an aqueous cosmetic composition which by adding at least one metabisulfite thereto.

12 Claims, No Drawings

SINGLE-PHASE TRANSPARENT AQUEOUS COSMETIC COMPOSITION

BACKGROUND OF THE INVENTION

1. Field of the Invention

The present invention relates a single-phase transparent aqueous liquid cosmetic composition comprising at least one metabisulfite and at least one alkyl para-hydroxybenzoate (paraben), and to the use of the composition for gently cleaning and/or removing make-up from the skin and/or eyes. Another subject-matter of the invention is a process for dissolving an alkyl para-hydroxybenzoate in an aqueous cosmetic composition by adding at least one metabisulfite thereto.

2. Discussion of the Background

Single-phase (monophase) transparent aqueous liquid compositions are compositions which do not comprise an oily phase and which constitute cleaning and make-up removal lotions. These lotions are commonly used in the cosmetics field, in particular for completing the removal of make-up from the skin and/or eyes after the use of a milk. They comprise a large amount of water and constitute, for example, toning lotions and make-up removers for the eyes.

These monophase aqueous liquid compositions comprise preservatives, in particular alkyl para-hydroxybenzoates, also known as parabens. These parabens, and in particular methylparaben, which are widely used in cosmetics for their antifungal properties, exhibit the disadvantage of having very little solubility in aqueous medium. In fact, if they are not entirely dissolved the parabens have a tendency to recrystallize, which is reflected by the formation of white particles. Such white particles have an unacceptable affect on the visual appearance and the sensorial quality of a transparent composition. In addition, in order to fully carry out their role of preservatives in the aqueous phase, the site of contamination, the parabens have to be completely dissolved in the aqueous phase.

It is therefore essential for the parabens to be entirely dissolved in the aqueous compositions, and in particular the transparent aqueous compositions, in order to achieve the greatest possible effectiveness and also in order to obtain perfect transparency of the composition.

One solution in promoting the solubilization of the parabens consists in adding a primary alcohol, such as ethanol, a polyol, such as a glycol, or a surfactant to the aqueous composition. However, the addition of primary alcohol is to be avoided, in particular in face lotions, because ethanol can have an irritating effect on skin. Furthermore, the addition of an excessively large amount of glycols confers a sticky and clinging nature on a liquid composition, such as a lotion. Moreover, the aim is to avoid the use of an excessively large amount of surfactants, due to their irritating nature with regard to the skin and eyes, in particular in sensitive subjects. In addition, some anionic and nonionic surfactants are incompatible with the parabens, the activity of which they inhibit.

The need therefore remains to have available a single-phase aqueous liquid cosmetic composition which does not have the disadvantages of known compositions and which is perfectly transparent by virtue of complete solubilization of the parabens.

SUMMARY OF THE INVENTION

The present invention is based on the Inventors' finding that, surprisingly, metabisulfites, and in particular sodium metabisulfite, make it possible to obtain entirely transparent aqueous compositions in which the parabens, and in particular methylparaben, are completely dissolved. The final product has good stability and protection from microbiological growth.

Accordingly, the present invention relates to a single-phase transparent aqueous liquid cosmetic composition, which comprises:

- at least one alkyl para-hydroxybenzoate, where the alkyl group has from 1 to 6 carbon atoms,
- at least 90% by weight of water with respect to the total weight of the composition, and
- at least one metabisulfite, where the amount of metabisulfite is at the most of 0.02% by weight with respect to the total weight of the composition.

A more complete appreciation of the invention and many of the attendant advantages thereof will be readily obtained as the same becomes better understood by reference to the following detailed description.

DETAILED DESCRIPTION OF THE INVENTION

As used herein, the term "transparent" means that it is possible to distinguish, through the bottle comprising the composition, the characters printed on a newspaper page placed behind this bottle. This term also means that a sample of the composition with a thickness of 10 cm has a maximum light transmission of at least 4% in any wavelength between 200 nm and 800 nm.

The term "liquid composition" as used herein refers to a composition comprising a high proportion of water and having a relative density of approximately 1, that is to say ranging from approximately 0.99 to 1.01. The composition of the invention comprises at least 90% by weight of water and preferably at least 95% by weight of water with respect to the total weight of the composition. The amount of water can range up to 99.9% by weight with respect to the total weight of the composition. These ranges include all specific values and subranges therebetween, such as 91%, 92%, 93%, 94%, 95%, 96%, 97%, 98%, 99% and 99.5% by weight.

It was unexpected that sodium metabisulfite, known for its antioxidizing properties, was capable of being used with success, even in small amounts, in dissolving parabens, thereby allowing good preservation to be obtained at the same time as perfect transparency, as well as excellent tolerance due to the use of quantities of metabisulfite which are sufficiently small (less than or equal to 0.02% by weight) to be non-irritating, which is particularly important for cosmetic use and especially for eye make-up remover.

Another subject-matter of the invention is consequently a process for dissolving an alkyl para-hydroxybenzoate in an aqueous cosmetic composition which consists in adding at least one metabisulfite.

The metabisulfite is generally a metal metabisulfite, such as an alkali metal metabisulfite, and preferably sodium metabisulfite. It is preferably present in an amount effective in ensuring the expected result and can be present, for example, in the composition according to the invention in an amount ranging from 0.001 to 0.02%, preferably from 0.002 to 0.01%, by weight with respect to the total weight of the composition. These ranges include all specific values and subranges therebetween, such as 0.005, 0.008 and 0.015% by weight with respect to the total weight of the composition.

In the alkyl para-hydroxybenzoate, the alkyl radical has from 1, 2, 3, 4, 5 or 6 carbon atoms and preferably from 1 to 4 carbon atoms. Examples of the alkyl para-hydroxybenzoate, include methyl para-hydroxybenzoate (methylparaben), ethyl para-hydroxybenzoate (ethylparaben), propyl para-hydroxybenzoate (propylparaben), butyl para-hydroxybenzoate (butylparaben) and isobutyl para-hydroxybenzoate (isobutylparaben).

In the composition of the invention, use is preferably made of methyl para-hydroxybenzoate, alone or as a mixture with one or more other parabens and/or with another preservative, such as phenoxyethanol. Use may be made, for example, of the mixture of methyl-paraben, ethylparaben, propylparaben and butylparaben sold under the name Nipastat by the company Nipa or the mixture of phenoxyethanol, methylparaben, ethylparaben, propylparaben and butylparaben sold under the name Phenonip by the company Nipa.

The alkyl para-hydroxybenzoate or the mixture of alkyl para-hydroxybenzoates is used in the composition according to the invention in an amount suited to the desired aim, i.e., good preservation of the composition from microorganisms. This amount can range, for example, from 0.01 to 1% and preferably from 0.05 to 0.5% by weight with respect to the total weight of the composition. These ranges include all specific values and subranges therebetween, such as 0.02, 0.03, 0.6 and 0.075% by weight with respect to the total weight of the composition.

The composition is preferably devoid of monohydric $C_1$–$C_3$ alcohol, and, in particular devoid of ethanol, the avoidance of the use of which is sought because of its irritant and skin-inflaming nature. Likewise, the composition is preferably devoid of gelling agents.

The composition of the invention can comprise one or more polyols and in particular glycols in an amount such that it does not confer a clinging nature on the final composition. Mention may particularly be made, among the polyols which can be used in the composition according to the invention, of propylene glycol, butylene glycol, glycerol, hexylene glycol, polyethylene glycols, such as PEG-8, dipropylene glycol and their mixtures. The amount of polyol (s) in the composition of the invention generally ranges from 0.1 to 9.5% and preferably from 1 to 5% by weight with respect to the total weight of the composition. These ranges include all specific values and subranges therebetween, such as 0.2, 0.5, 0.75, 1.25, 1.5, 2, 3 and 8% by weight with respect to the total weight of the composition The aqueous liquid composition of the invention may, optionally, comprise a surfactant, the presence of which makes it possible to improve the removal of make-up. This surfactant is generally present in an amount ranging from 0.01 to 5% and more preferably still from 0.05 to 2% by weight with respect to the total weight of the composition. These ranges include all specific values and subranges therebetween, such as 0.02, 0.075, 1.25, 3 and 4% by weight with respect to the total weight of the composition.

Mention may be made, as surfactant which can be used in the composition of the invention, of sodium laureth sulfate, such as the product Texapon ASV® sold by Henkel, disodium cocoamphodiacetate, such as the product Miranol 2CM® sold by Rhodia Chimie, polysorbates, and poloxamers, such as the products sold by ICI under the name of Synperonic.

In the composition of the invention, the water used can be pure demineralized water but also mineral water and/or thermal water, that is to say that the water of the composition can be partially or entirely composed of a water chosen from mineral and/or thermal waters. In general, a mineral water is fit for consumption, which is not always the case with a thermal water. Each of these waters contains, inter alia, dissolved minerals and/or trace elements. These waters are known to be employed for specific treatment purposes, depending on the specific trace elements and minerals which they comprise, such as moisturization and desensitization of the skin or the treatment of certain dermatoses. The term "mineral or thermal waters" will be understood to denote not only natural mineral or thermal waters but also natural mineral or thermal waters enriched in additional mineral constituents and/or trace elements, as well as aqueous mineral and/or trace-element solutions prepared from purified water (demineralized or distilled water).

A natural thermal or mineral water used according to the invention can, for example, be chosen from water from Vittel, waters from the Vichy basin, water from Uriage, water from La Roche Posay, water from La Bourboule, water from Enghien-les-Bains, water from Saint Gervais-les-Bains, water from Neris-les-Bains, water from Allevar-les-Bains, water from Digne, water from Maizieres, water from Neyrac-les-Bains, water from Lons-le-Saunier, water from Eaux-Bonnes, water from Rochefort, water from Saint Christau, water from Fumades, water from Tercis-les-Bains and water from Avene.

The cosmetic compositions of the invention are intended for a topical application and appropriately comprise a physiological acceptable medium. The term physiologically acceptable medium is understood to mean a medium which is compatible with the skin, the mucous membranes (including the inside of the eyelids and the lips), the nails and/or the keratinous fibres (hair and eyelashes). These compositions can additionally comprise standard adjuvants in the cosmetics field, such as antioxidants, fragrances, screening agents, colouring materials, or hydrophilic or lipophilic active principles. The nature of the adjuvants and their amounts must be such that they do not modify the properties of the composition according to the invention. The amounts of these adjuvants are those conventionally used in the cosmetics field, for example from 0.001 to 5% of the total weight of the emulsion.

In one embodiment, the compositions of the invention are in the form of lotions particularly suited to cleaning and/or removing make-up from the skin and/or eyes.

Another subject-matter of the invention is consequently the cosmetic use of the composition as defined above for cleaning and/or removing make-up from the skin and/or eyes. Here, the composition is applied to the area desired to be treated. The area may also be rinsed with water after applying the composition in order to further cleanse the skin.

EXAMPLES

Having generally described this invention, a further understanding can be obtained by reference to certain specific examples which are provided herein for purposes of illustration only and are not intended to be limiting unless otherwise specified.

EXAMPLE 1

Lotion for Cleaning the Face and Eyes

| | | |
|---|---|---|
| Glycerol | | 3% |
| Sodium metabisulfite | | 0.002% |
| Methylparaben | | 0.1% |
| Demineralized water | q.s. to | 100% |

The composition is prepared by mixing methyl-paraben and glycerol at 60° C. and by then introducing the mixture, with vigorous stirring and at room temperature, into water comprising sodium metabisulfite.

EXAMPLE 2

Lotion for Cleaning the Face and Eyes

| | | |
|---|---|---|
| PEG-8 | | 2% |
| Methylparaben | | 0.1% |
| Sodium metabisulfite | | 0.005% |
| Demineralized water | q.s. to | 100% |

The composition is prepared by mixing methyl-paraben and water at 80° C. and by then adding PEG-8 and sodium metabisulfite, with stirring and at room temperature, to the cooled mixture.

EXAMPLE 3

Lotion for Cleaning the Face and Eyes

| | | |
|---|---|---|
| Methylparaben | | 0.1% |
| Sodium metabisulfite | | 0.005% |
| PEG-8 | | 2% |
| Glycerol | | 3% |
| Cornflower water | | 1% |
| Demineralized water | q.s. to | 100% |

The composition is prepared by mixing methyl-paraben and glycerol at 60° C. and by then introducing the mixture into water with vigorous stirring at room temperature. When the solution is clear, sodium metabisulfite, PEG-8 and cornflower water are added, each ingredient being introduced successively with stirring and at room temperature.

Obviously, numerous modifications and variations of the present invention are possible in light of the above teachings. It is therefore to be understood that within the scope of the appended claims, the invention may be practiced otherwise than as specifically described herein.

This application is based on French Patent Application Serial No. 98-09301, filed on Jul. 21, 1998, and incorporated herein by reference.

What is claimed is:

1. A transparent aqueous cosmetic composition, consisting essentially of:

a single-phase aqueous formulation of alkyl para-hydroxybenzoate dissolved in at least 90% by weight of water, from 0.001 to 0.02% by weight of sodium metabisulfite, and a polyol selected from the group consisting of propylene glycol, butylene glycol, hexylene glycol, polyethylene glycols, glycerol, dipropylene glycol and mixtures thereof, all percentages based on the total weight of the composition, which cleans, removes make-up or both from the skin, eyes or both.

2. The transparent aqueous cosmetic composition according to claim 1, further consisting essentially of 0.01–5% by weight of a surfactant.

3. The transparent aqueous cosmetic composition according to claim 2, wherein the amount of surfactant ranges from 0.05–2% by weight of a surfactant.

4. The transparent aqueous cosmetic composition according to claim 1, wherein the content of water in the composition is at least 95% by weight.

5. The transparent aqueous cosmetic composition according to claim 1, wherein the content of alkyl para-hydroxybenzoate ranges from 0.01 to 1% by weight.

6. The transparent aqueous cosmetic composition according to claim 5, wherein the content of alkyl para-hydroxybenzoate ranges from 0.05 to 0.5% by weight and the content of polyol ranges from 0.1 to 9.5% by weight.

7. A transparent aqueous cosmetic composition, consisting essentially of:

a single-phase aqueous formulation of methyl para-hydroxybenzoate dissolved in at least 90% by weight of water, from 0.001 to 0.02% by weight of sodium metabisulfite, and glycerol, PEG-8 or a mixture thereof, all percentages based on the total weight of the composition, which cleans, removes make-up or both from the skin, eyes or both.

8. The transparent aqueous cosmetic composition according to claim 7, further consisting essentially of 0.01–5% by weight of a surfactant.

9. The transparent aqueous cosmetic composition according to claim 8, wherein the amount of surfactant ranges from 0.05–2% by weight of a surfactant.

10. The transparent aqueous cosmetic composition according to claim 7, wherein the content of water in the composition is at least 95% by weight.

11. The transparent aqueous cosmetic composition according to claim 7, wherein the content of alkyl para-hydroxybenzoate ranges from 0.01 to 1% by weight.

12. The transparent aqueous cosmetic composition according to claim 11, wherein the content of alkyl para-hydroxybenzoate ranges from 0.05 to 0.5% by weight and the content of polyol ranges from 0.1 to 9.5% by weight.

* * * * *